United States Patent [19]

DeCant, Jr. et al.

[11] 4,447,224

[45] May 8, 1984

[54] VARIABLE FLOW IMPLANTABLE INFUSION APPARATUS

[75] Inventors: Leonard J. DeCant, Jr., Allston; Samir F. Idriss, Arlington; Frank R. Prosl, Duxbury, all of Mass.

[73] Assignee: Infusaid Corporation, Norwood, Mass.

[21] Appl. No.: 419,733

[22] Filed: Sep. 20, 1982

[51] Int. Cl.$^3$ .............................................. A61M 5/14
[52] U.S. Cl. ....................................... 604/67; 138/26; 128/DIG. 13; 128/DIG. 12
[58] Field of Search ............................ 604/141, 65, 67; 73/721; 92/44; 128/DIG. 13, DIG. 12, DIG. 1; 138/26; 222/52, 55

[56] References Cited

U.S. PATENT DOCUMENTS

| | | | |
|---|---|---|---|
| 3,450,153 | 6/1969 | Hildebrandt et al. | 604/65 |
| 3,529,908 | 9/1970 | Smith | 92/44 |
| 3,731,681 | 5/1973 | Blalkshear et al. | 222/386.5 |
| 3,936,028 | 2/1976 | Norton et al. | 251/5 |
| 3,961,646 | 6/1976 | Schön | 138/26 |
| 3,985,133 | 10/1976 | Jenkins et al. | 604/67 |
| 4,237,900 | 12/1980 | Schulman et al. | 128/736 |
| 4,364,276 | 12/1982 | Shimazoe et al. | 73/721 |
| 4,376,523 | 3/1983 | Goyen | 251/145 |
| 4,395,258 | 7/1983 | Wang et al. | 604/67 |

Primary Examiner—William E. Kamm
Assistant Examiner—Steven Falk
Attorney, Agent, or Firm—Cesari and McKenna

[57] ABSTRACT

Implantable variable flow infusion apparatus comprises a collapsible infusate chamber having an outlet conduit leading to the infusion site by way of series-connected fixed and variable fluid flow restrictors. The infusate in the chamber is maintained under substantially constant pressure by a nonelectric energy storage cell to establish flow from the chamber to the site. The variable restrictor is controlled by commands from a preprogrammed microprocessor and programmable memory powered by a small long-lived battery. The processor sets the variable restrictor to the proper setting to establish the correct infusate flow for the particular time of day. A pressure transducer connected across the fixed restrictor senses the pressure differential across the fixed restrictor which differential indicates actual infusate flow from the chamber. The processor samples the output from the transducer at infrequent sampling intervals and issues command signals to control the variable restrictor whenever the actual infusate flow rate differs from the preprogrammed rate so that the apparatus consumes a minimal amount of battery energy and can thus remain implanted in the body for a prolonged period. The processor can also be reprogrammed and monitored by telemetry.

20 Claims, 3 Drawing Figures

VARIABLE FLOW IMPLANTABLE INFUSION APPARATUS

This invention relates to implantable infusion apparatus. It relates more particularly to apparatus of this type which automatically dispenses infusate to a patient at flow rates which may be varied depending upon the patient's needs.

BACKGROUND OF THE INVENTION

In recent years, infusion apparatus has been developed which can be implanted in the body and remain there for a prolonged period. The apparatus can be refilled with infusate without having to remove the apparatus from the patient's body by injecting additional infusate through a penetrable septum in the apparatus wall located directly under the patient's skin. Examples of infusion apparatus of this general type are disclosed in U.S. Pat. Nos. 3,731,681 and 3,951,147.

In the treatment of some patients such as those afflicted with diabetes, the amount of medication such as insulin infused per unit of time should be adjusted at certain time intervals. This is because the patient's requirements may fluctuate during the day, such fluctuations being caused, for example, by the ingestion of food or by some other transitory condition calling for the administration of a bolus dose of infusate. Some prior implantable infusion devices provide this flexibility, examples being shown in U.S. Pat. Nos. 3,894,538 and 4,077,405.

It has also been proposed to program the daily administration of medication such as insulin. In such apparatus, an infusate injector is moved by a motor drive in accordance with a program in such a way that the desired daily dose is achieved while accounting for fluctuations in the patient's glucose level, temperature and ambient pressure to which the patient is subjected. See, for example, U.S. Pat. No. 4,003,379 and the references cited therein.

The aforesaid implantable infusion apparatus is disadvantaged in one or another of the following respects. Some of the devices of this general type have an excessive energy requirement, either to develop the necessary pressure to dispense the infusate to the patient or to regulate the flow to provide the desired dosages. If the energy requirement is supplied by a battery, that battery has to be replaced or recharged relatively often, requiring, at the very least, penetration of the patient's skin, giving rise to the possibility of infection.

Also, some such prior apparatus only dispense infusate to the patient intermittently or periodically which is disadvantageous in some instances. For example, tests have shown that diabetics should receive a basal dose of insulin which is continuous, with the basal dose being supplemented by so-called bolus doses at certain times of the day, such as at mealtimes. The difference in the basal and bolus flow rates may be several orders of magnitude, and it is quite difficult to achieve proper flow control over that entire range of flow rates. The device disclosed in U.S. Pat. No. 4,140,112 does have the advantage of achieving a continuous dosing of infusate even at very small flow rates. However, that continuous feeding or injection of medication also requires a continuous generation of pressure and consequently a higher requirement of input energy for the electrodes which control infusate flow. Furthermore, that requirement increases substantially when the flow rate of medication is increased.

Also, some such apparatus do not maintain a high enough accuracy of the dose rate with variations in environmental and physiological conditions such as temperature and pressure. Also, some are relatively complicated in their design and control. In other words, they require an excessive number of mechanical components. This renders it impractical to manufacture such devices with the required small size to enable them to be implanted in the patient's body without undue discomfort to the patient.

In general, the prior comparable devices of which we are aware do not take into account all of the physiological concepts and clinical factors involved in the various therapies, particularly diabetes therapy, in connection with which such implantable devices are used. In general, such apparatus should have the following attributes:

1. continuous drug delivery;
2. adjustable infusate flow rate with programmability of rate choices;
3. a large range of flow rate choices;
4. a high accuracy of dose rate, maintained constant with variations in environmental and physiological conditions;
5. simplicity of operation, design and control;
6. low system operating pressures;
7. low infusate operating pressures, thereby providing a low shear in the infusate being delivered;
8. a low power consumption;
9. a long life;
10. the ability for in vivo monitoring and verification of dose rate;
11. a built-in fail-safe mode of operation; and
12. a long refill period.

SUMMARY OF THE INVENTION

Accordingly, the present invention aims to provide improved implantable infusion apparatus which has all of the above abilities and is thus particularly adapted for use in connection with various therapies, particularly diabetes therapy.

Another object of the invention is to provide such infusion apparatus which delivers a continuous flow of infusate to the patient at precisely controlled very low flow rates and at higher rates which may vary over a wider range.

A further object of the invention is to provide apparatus of this type which can be programmed either externally or internally to vary the infusate dosage to the patient.

Still another object of the invention is to provide implantable infusion apparatus which delivers the programmed infusate dose to the patient despite changes in the atmospheric pressure to which the patient is subjected or changes in patient temperature.

Another object of the invention is to provide such apparatus whose components can be contained in a relatively small package so that its implantation in a patient does not produce undue discomfort to the patient.

Yet another object of the invention is to provide implantable infusion apparatus having a minimum energy requirement so that it can remain operative in the patient for a prolonged period, e.g. on the order of ten years or more.

A further object of the invention is to provide apparatus of this type which operates in a fail-safe mode so that there is no danger of the patient suffering an infusate overdose.

A further object of the invention is to provide apparatus which monitors the actual flow rate and pump conditions enabling flow corrections to be made by providing a feedback control mode of operation.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, the components of our apparatus are all contained in a relatively small hermetically-sealed housing made of a biocompatible material. These components include a pressurized infusate chamber which dispenses infusate to a catheter at the infusion site by way of series-connected fixed and variable flow restrictors. The flow rate of the infusate from the infusate chamber to the catheter is governed by the pressure differential across the two restrictors and the resistance of the restrictors. A transducer connected across the fixed restrictor measures the pressure drop across that restrictor and that drop is compared in a microprocessor with a reference pressure drop corresponding to the desired flow rate stored in a programmable memory associated with the processor. The processor provides control signals to an actuator which varies the flow resistance of the variable flow restrictor until the desired pressure drop across the fixed restrictor and hence the desired infusion rate is attained. A telemetry transceiver in the housing is connected to the memory and processor so that a programming unit outside the body can be used to input and initiate the desired flow rate schedules to the programmable memory using RF telemetry.

The present apparatus is designed to minimize energy consumption, while accurately maintaining a wide variety of constant flow rates. In this, the transducer only samples the operating pressure differential intermittently to verify the selected flow rate. The energy storage element which pressurizes the infusate chamber maintains the pressure in that chamber constant to the desired degree of precision between the sampling periods. A change in the infusate flow rate, either to initiate a bolus delivery of drug or to maintain the selected basal flow rate is accomplished by coarsely adjusting the variable restrictor to a precalibrated coarse "setting" and then using the transducer to verify that setting. Thus power is used to activate the electromechanical actuator controlling the variable flow restrictor only to select a particular flow rate or to verify that flow rate. By properly choosing the energy storage element, the sampling frequency can be minimized. To put it another way, the energy storage element which pressurizes the infusate chamber provides all of the energy to pump the infusate to the catheter and that storage element is totally rechargeable. Electrical power is used only to alter or to verify the infusate flow rate at infrequent intervals and to maintain a low level of current to the electronics.

The variable restrictor is designed to regulate and maintain its preset flow rate to the desired precision as the outlet catheter pressure changes with atmospheric and physiological conditions. Thus, a selected constant infusate flow is maintained between sampling periods.

If the infusate being dispensed is of a type that is adversely affected by passage through a flow restrictor, the infusate can be delivered from the infusate chamber directly to the catheter and the regulation of that flow rate achieved by regulating the rate of flow of a secondary, more viscous control fluid from one reservoir to another through the series-connected flow restrictors. In this embodiment, the transducer monitors the pressure drop across the fixed restrictor of the control fluid and the resistance of the variable flow restrictor is varied to vary the flow rate of the control fluid and thus the flow rate of the infusate.

By the use of an external transmitter, various desired infusate flow rates may be transmitted telemetrically to the transceiver located in the apparatus housing and that data stored in the programmable memory. A comparison of those values with the value obtained by monitoring the control fluid flow rate as aforesaid determines whether or not the proper infusate flow rate control has been established at any given time. If that flow rate is not the desired one, the resistance of the variable flow restrictor is changed to produce the desired infusate flow rate from the chamber.

Subcutaneous access to the interior of the infusate chamber for refilling purposes is had by way of a penetrable septum in the housing wall which, when the apparatus is implanted, is located directly under the patient's skin. The process of refilling the chamber also recharges the energy storage element which pressurizes that chamber. Therefore, the apparatus can remain implanted in the body for several years.

With apparatus such as this used to control a life-dependent physiological event, safety is of the highest priority. Accordingly, the present apparatus includes an electrically controlled, fail-safe valve in the outlet line from the infusate chamber. The microprocessor in the apparatus utilizes the pressure differential signal developed by the transducer for safety monitoring purposes. If that differential deviates from the desired value for a predetermined time interval, the microprocessor issues a command signal which automatically closes that valve, thereby discontinuing infusate flow to the patient. That valve can also be designed to be actuated externally using a magnet or a subcutaneous electric button, for example. Accordingly, if there were catastrophic failures of both the electronic and mechanical components of the apparatus, the patient would still be able to discontinue the infusate flow manually.

The processor can also be programmed to close that valve when the infusate chamber is being refilled.

Thus the present apparatus possess all of the requirements for a successful implantable infusate pump. It can be programmed externally and noninvasively by a physician, allowing its output to be matched to patient infusate demands. Further, continuous monitoring of the pump's operation and its inherent data storage allows the physician to determine and verify certain parameters such as the flow rate and quantity of insulin delivered to the patient during a particular operating cycle. Likewise, the apparatus permits a certain amount of patient control. For example, in the case of insulin infusate, it permits the patient to initiate the higher bolus mealtime rate and to change that rate according to certain requirements, for example, to match his caloric intake during each meal.

Thus, the advantages of the present apparatus include continous infusate delivery, adjustable infusate flow rate with programmability of rate choices, a large range of flow rate choices, high accuracy of dose rate, maintained constant with variations in environmental and physiological conditions; simplicity of operation, design and control; low system operating pressure; a low energy/power consumption; a long life; the ability for in vivo monitoring and verification of dose rate; a long refill period and built-in fail-safe operation.

BRIEF DESCRIPTION OF THE DRAWINGS

For a fuller understanding of the nature and objects of the invention, reference should be had to the following detailed description, taken in connection with the accompanying drawings, in which.

DESCRIPTION OF THE PREFERRED EMBODIMENTS

Figure 1:
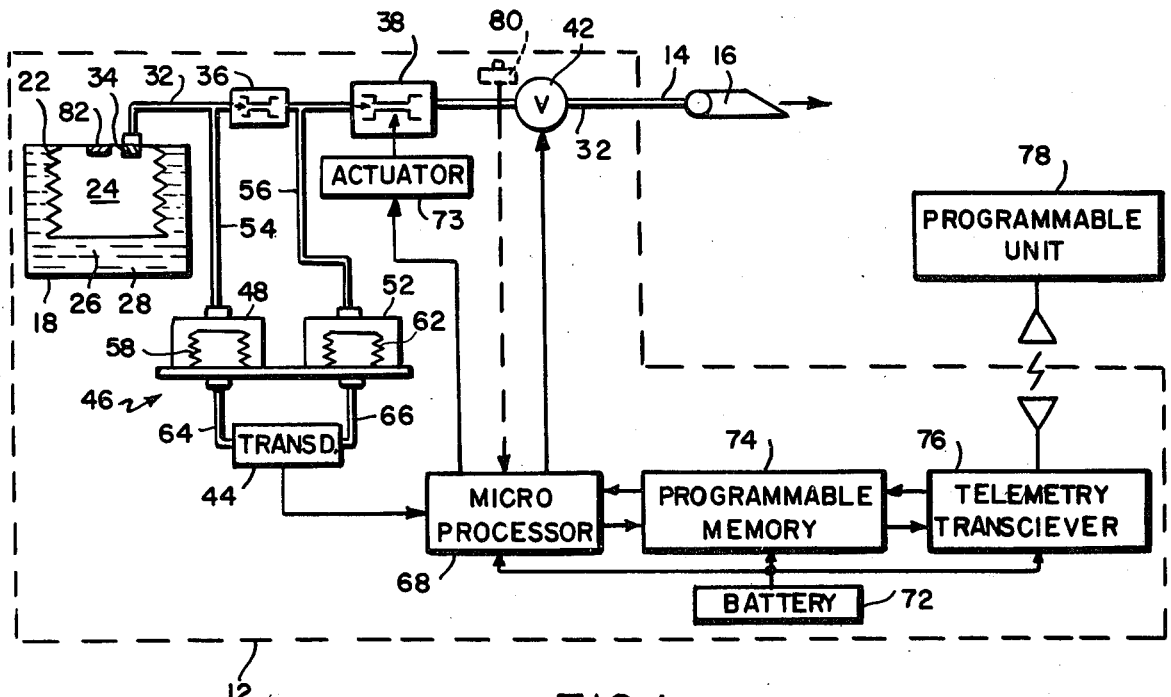
FIG. 1 is a diagrammatic view illustrating variable-flow implantable infusion apparatus embodying the principles of this invention.

Referring to FIG. 1 of the drawing, our apparatus comprises a relatively small compact housing shown in dotted lines at 12 made of a suitable biocompatible material such as titanium metal. Preferably, that housing is coated with a plastic material (not shown) such as silastic, which is also compatible with the human system. The illustrated apparatus, which may be used to dispense insulin to a diabetic patient, is shaped like a hockey puck and is on the order of ⅜" thick and has an outside diameter of about 3 ⅞".

In use, the apparatus is implanted in a patient's subdermal cavity created in the upper chest and tied to the chest muscles. The apparatus delivers infusate to the patient by way of a flexible outlet tube 14 made of silicone rubber, for example, to a catheter 16 which is inserted into an appropriate infusion site in the patient's body, say, the superior vena cava, by way of the upper subclavian vein. The basic construction of the housing 12 is depicted in the aforesaid U.S. Pat. No. 3,731,681.

Positioned inside housing 12 is a container 18 enclosing a metal bellows capsule 22 mounted to its top wall. Capsule 22 defines an infusate chamber 24. Also, the space outside capsule 22 but inside container 18 constitutes a second closed chamber 26. That chamber is filled with a two-phase fluid 28 which vaporizes at physiological temperatures so that it constitutes a power cell or energy storage element. Such power cells are well known and are fully disclosed in the aforesaid patents. Basically, the fluid 28 evaporates at body temperature so as to exert a substantially constant force on the capsule 22 tending to collapse it. The infusate therein is expelled from chamber 24 through an outlet conduit 32. A filter 34 at the entrance to that conduit excludes dirt from the conduit. Conduit 32 communicates with outlet tube 14 by way of a fixed fluid flow restrictor 36, a variable fluid flow restrictor 38 and an electromechanical valve 42, all of those components being connected together in series.

Still referring to FIG. 1, a differential pressure transducer 44 is connected in parallel with the fixed flow restrictor 36 by way of an isolation assembly indicated generally at 46. The purpose of the isolation assembly is to protect the patient from an infusate overdose in the event there should be a leakage failure of transducer 44 and to isolate the transducer from corrosive infusate solutions. That assembly comprises a pair of chambers 48 and 52 connected by conduits 54 and 56 to conduit 32 at opposite sides of restrictor 36. Positioned in container 48 is a deformable chamber in the form of a bellows capsule 58. A similar capsule 62 is contained in chamber 52. The interiors of capsules 58 and 62 are connected by conduits 64 and 66 respectively to the opposite sides of transducer 44. Chambers 48 and 52 and their connecting conduits 54 and 56, being in communication with conduit 32, are filled with infusate. On the other hand, the capsules 58 and 62 as well as their conduits 64 and 66 communicating with transducer 44 are filled with an inert incompressible fluid such as dimethylpolysiloxane solution which is compatible with the transducer materials and the human system should a leak occur. The transducer 44 may comprise, for example, a container divided into two compartments by a piezoresistive bender whose electrical resistance is proportional to its flexure due to the pressure difference across it. That resistance value is applied to a microprocessor 68 powered by a miniature long-lived battery 72 which may be, for example, a lithium-iodide cell which has a useful life of three years or more. The microprocessor issues control signals to an electromechanical actuator 73 which controls the variable flow restrictor 38. Signals from the microprocessor are also used to control the opening and closing of the valve 42 at the appropriate times.

Microprocessor 68 is programmed by data stored in a programmable memory 74. The data in the memory is updated and retrieved by a telemetry transceiver 76 which receives the data from and transmits it to a programmable unit 78 located outside the patient's body using RF telemetry. Both memory 74 and transceiver 76 are also powered by battery 72.

During normal operation of the apparatus, the infusate chamber 24 is filled with infusate which is maintained under a substantially constant pressure by the power cell in chamber 26. The transducer 44 senses the pressure differential between bellows capsules 58 and 62. That pressure differential, in turn, represents the pressure drop across the fixed flow restrictor 36, which drop is indicative of the actual infusate flow rate from chamber 24 to catheter 16. Microprocessor 68 samples the output of transducer 44 at selected time intervals as determined by programmed instructions stored in memory 74. The processor 68 computes from that resistance value the actual infusate flow rate and compares that rate with the programmed flow rate for the particular time of day which is stored in memory 74. If the actual infusate flow rate is correct, no command signal is issued to control the variable restrictor 38. If, on the other hand, the sampled pressure differential is too high or too low, the processor issues an appropriate command signal to actuator 73 to close or open restrictor 38 until the actual infusate flow rate equals the programmed one.

From that point on, the aforesaid process of sampling the pressure differential across restrictor 36 and comparing the calculated actual flow rate to the desired one is repeated only at appropriate sampling intervals as determined by the program in processor 68. The variable flow restrictor 38 is actuated only when the pressure differential deviates from a preset error limit programmed into the microprocessor. This control technique is designed to be much less power intensive than continuous feedback control.

If the patient's infusion schedule calls for a change in the infusate dosage, the processor 68 issues a command signal to actuator 73 which opens or closes restrictor 38 to achieve a coarse setting of that new flow rate. Then the processor goes through its sampling routine and samples the pressure differential across restrictor 36, comparing the sampled value with the programmed value of the new flow rate and uses that data to control restrictor 38 to achieve a fine setting of the new flow rate.

For example, in the case of insulin, the dosage schedule programmed into the processor 68 might call for a certain basal infusate flow rate for a 24-hour day. Then, at certain times during the day, say, during the normal mealtime periods, the program may call for that basal flow to be supplemented by a higher bolus flow to compensate for the patient's increased glucose intake during those times. Accordingly, at the proper time for a bolus dose, the processor 68 controls restrictor 38 so that the restrictor opens sufficiently to permit the higher bolus flow rate. Then the processor 68 samples the output from transducer 44 and compares the sampled value with the desired bolus flow value programmed into the processor memory 74 and issues command signals to the actuator 73 at successive sampling intervals until the desired bolus flow is achieved within the error limit programmed into the processor.

At the end of a prescribed one-hour time period, the processor 68 issues a command causing the restrictor 38 to become more restrictive, thereby achieving a coarse resetting of the basal infusate flow rate. Again, the pressure differential across restrictor 36 is sampled and that information used to control restrictor 38 until the normal basal flow of infusate to catheter 16 is re-established.

It is important to note that the present apparatus consumes energy from battery 72 only when setting a particular infusate flow rate and when intermittently sampling the output of transducer 44, which reflects the operating pressure differential, to verify that the actual flow rate is indeed the programmed one and to maintain low level power to the electronics. All of the energy required to deliver or dispense the infusate is provided by the power cell in chamber 26. The power cell provides all of the energy to pump the infusate and is totally rechargeable. The variable restrictor 38 to be described in detail presently is designed to regulate and maintain its preset flow rate to the desired precision as catheter 16 pressure changes with atmospheric and physiological conditions.

When the supply of infusate in chamber 24 is depleted, the physician sends a telemetry signal to transceiver 76 which causes processor 68 to shut valve 42 so that there is no infusate flow to the patient. Then chamber 24 is refilled by inserting a hypodermic needle through the septum 82 which communicates with chamber 24. The fresh infusate flows into chamber 24 causing the bellows capsule 22 to extend. The extension of bellows 22 compresses and condenses the two-phase fluid 28 in chamber 26, thereby recharging the power cell. As soon as the refilling process is completed and the valve 42 reopened, the recharged and refilled apparatus recommences its controlled dispensing of infusate to the patient.

The valve 42 also serves a fail-safe function. More particularly, if the pressure differential across restrictor 36 as measured by transducer 44 deviates from the desired value for a preset number of samples, this is recognized by the microprocessor 68. The processor thereupon issues a command signal to close valve 42, thereby discontinuing infusate flow to the infusate site.

Valve 42 can also be designed to have a manual actuation capability with the valve being closed by a subcutaneous electrical switch mounted in the top wall of housing 12 as shown in dotted lines at 80 in FIG. 1. The switch is connected electrically to processor 68 and actuated by pressing against the skin or by a magnet positioned outside the patient's body opposite the switch. See, for example, U.S. Pat. No. 4,193,297. Thus, even if there is a catastrophic failure of both the electronic and mechanical subsystems in the present apparatus, the patient himself would still be able to discontinue manually the infusate flow to catheter 16.

Such valve 42 can also be operated mechanically or magnetically to close in the event of catastrophic electrical failure, e.g. battery failure.

Such a switch could also be used to enable the patient to control the processor 68 to switch between the basal and bolus flow rates at times which he himself can select. For example, one depression of switch 80 might cause processor 68 to switch to the bolus flow rate program; a second depression might cause it to resume the basal program; three and four depressions of the switch might cause the processor 68 to respectively close and open valve 42. Likewise, a simpler version of the programming unit 78 could be used to provide a certain amount of patient control over pump operation.

If at any time it is desired to change the dosage schedule for a particular patient, the microprocessor 68 can be reprogrammed by means of the telemetry transceiver 76. This simply involves transmitting coded data by means of a programmable telemetry transceiver unit 78 positioned outside the patient's body opposite the antenna of the implanted transceiver 76. Apparatus for transmitting telemetry data to a device implanted in the human body is well-known, an example of same being disclosed in U.S. Pat. No. 4,077,405.

The processor 68 and memory 74 can also monitor and collect data relating to pump operation, such as flow rates, quantity of infusate dispensed over a given time period, battery condition, etc. Upon command from unit 78, this data can then be transmitted by transceiver 76 to the external unit 78 so that the physician will know that the apparatus is operating properly.

Figure 2:
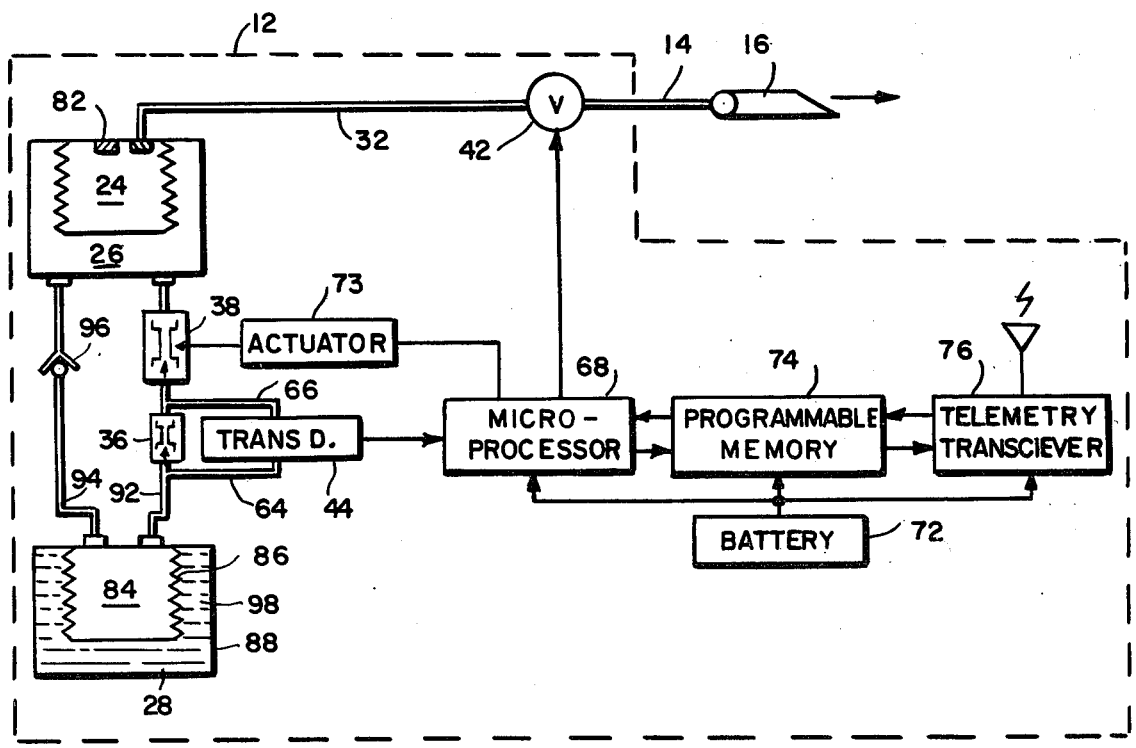
FIG. 2 is a similar view showing another apparatus embodiment.

Turning now to FIG. 2, in some applications, the particular infusate being dispensed might suffer adversely if it is required to flow through a restriction such as restrictors 36 and 38 in FIG. 1. Such restricted flow damages the molecules of such infusates and, in some cases, the infusate tends to clog the restricted flow paths. In the FIG. 2 apparatus, the infusate flow path from infusate chamber 24 to catheter 16 is completely unrestricted. Since the FIG. 2 apparatus is quite similar to the one depicted in FIG. 1, the components in common have the same identifying numerals.

In this embodiment, infusate flows from chamber 24 through an unrestriced conduit 32 directly to outlet tube 14 by way of the fail-safe valve 42. Instead of controlling infusate flow directly, it is controlled indirectly by regulating the flow of a control fluid between chamber 26 and a second pressure chamber 84 defined by a collapsible bellows capsule 86 positioned in a fluid-tight container 88. Chamber 26 is connected to chamber 84 by way of a conduit 92 containing the series-connected fixed restrictor 36 and variable restrictor 38. A by-pass conduit 94 containing a checkvalve 96 also communicates with chambers 26 and 84. The check valve 96 is normally closed when fluid is flowing from chamber 84 to chamber 26 and is opened when the flow is in the reverse direction, thereby shortcircuiting the flow restrictors 36 and 38 when the chamber 24 is being refilled with infusate. The chambers 26 and 84 and their connecting conduits are filled with a pressure-transmitting medium having a low viscosity vs. temperature coefficient as compared with that of the infusate. One suitable pressure transmitting medium is dimethylpolysiloxane. The chamber 98 outside bellows capsule 86 and inside container 88 is filled with the two-phase fluid 28 which functions as a power cell as described above.

As before, the pressure differential across the fixed restrictor 36 is measured by a transducer 44. In this case, however, the isolating assembly 46 depicted in FIG. 1 is not required since infusate is not flowing through that line. Rather the conduits 64 and 66 from the transducer are connected directly to conduit 92 at opposite sides of the flow restrictor 36.

The pressure differential across restrictor 36 is monitored by transducer 44 and the output of the transducer is sampled by processor 68 as described above. The processor through a conventional programmed algorithm processes that information to develop the actual control fluid flow rate from chamber 84 to chamber 26.

The flow rate from the infusate chamber 24 is related to the flow rate of the control fluid in that the control fluid volume exactly displaces (in a one-to-one ratio) the infusate volume. Therefore, the microprocessor 68 can calculate the actual infusate flow rate from chamber 24 to catheter 16. During each sample interval, the processor compares this value with the programmed flow rate for the particular time of day as described earlier. If the sampled rate is correct, no command signal is issued by the processor to control restrictor 38. On the other hand, if the sampled rate differs from the programmed one, the processor 68 opens or closes restrictor 38 as needed to achieve the correct flow rate.

The FIG. 2 apparatus has all of the advantages of the one described in connection with FIG. 1. In addition, the viscosity of the control fluid in chambers 26 and 84 and their connecting conduits may be much higher than that of the infusate in chamber 24. Therefore, relatively large tubing can be used as the conduit 92 between chambers 26 and 84. Accordingly, the flow rate of that fluid can be controlled very precisely over a wide range. Also as noted above, the control fluid may be selected to have a very low viscosity vs. temperature coefficient so that its flow characteristics do not change appreciably with changes in the patient's temperature. On the other hand, pressure changes to which the patient is subjected are reflected in a change in the pressure differential across the restrictor 36 and therefore are compensated for by the microprocessor control of the variable restrictor 38. Further, as mentioned previously, the infusate has an unrestricted flow path to the patient.

Figure 3:
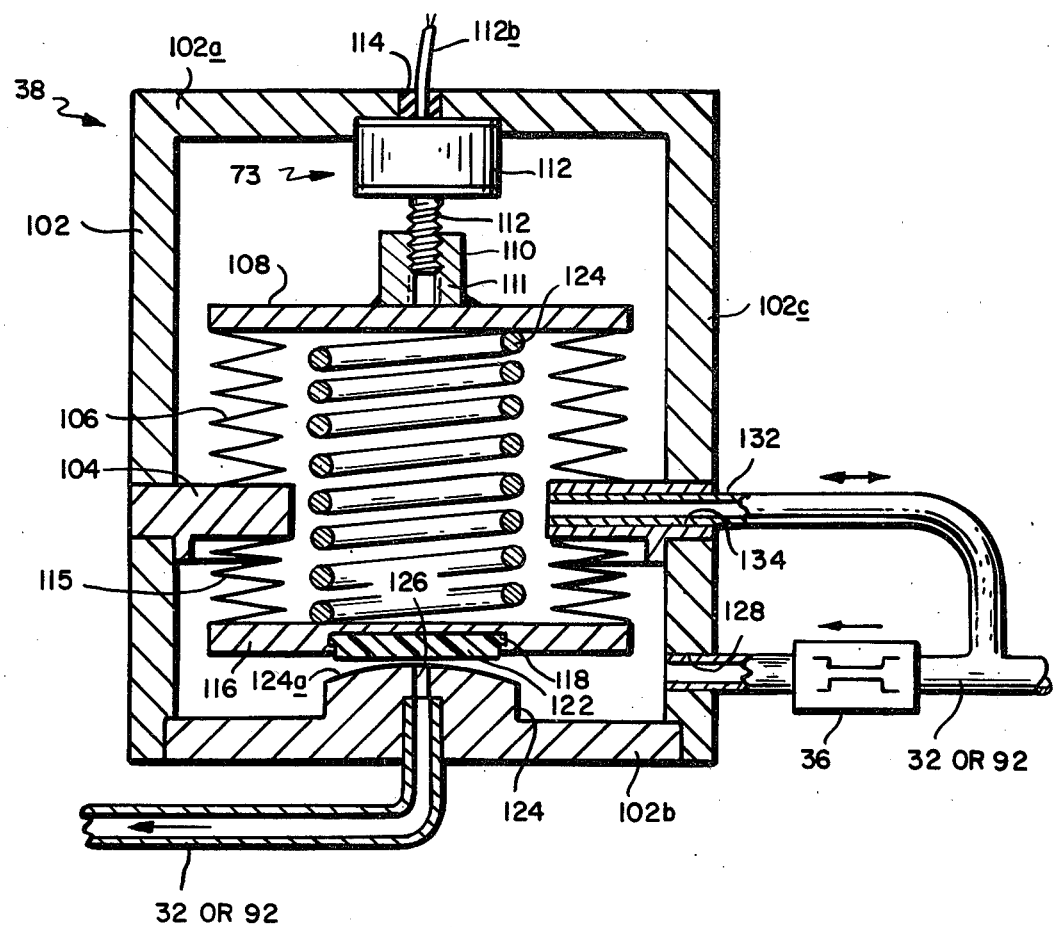
FIG. 3 is a sectional view illustrating a part of the apparatus in greater detail.

Turning now to FIG. 3, the variable flow restrictor 38 comprises a generally cylindrical housing 102 having a top wall 102a, a bottom wall 102b and a cylindrical side wall 102c. An annular dividing wall 104 divides the housing into upper and lower compartments. Positioned in the upper compartment is a bellows capsule 106 having one end sealed to dividing wall 104 and its opposite end closed by a discoid plate 108. Projecting up from plate 108 is a collar 110 having an internally threaded bore 111. Mounted to the underside of the housing top wall 102a is a small electric stepping motor 112 whose output shaft 112a is threadedly received in bore 111. The motor 112 has electrical leads 112b which extends out of the housing through a feedthrough 114 in the housing top wall 102a. Step motor 112 constitutes the actuator 73 in FIGS. 1 and 2.

Positioned in the lower housing compartment is a second bellows capsule 115 having one end sealed to the underside of dividing wall 104 and its opposite end closed by a discoid plate 116. Plate 116 has an axial recess 118 in which is seated a resilient discoid seal 122. Compressed between end plates 108 and 116 is a coil spring 124 which extends through the central opening 104a in the annular divider wall 104. The position of the upper end plate 108 is fixed by the motor shaft 112a so that the spring 124 exerts a downward force on plate 116 forcing it against a boss 124 projecting up from the housing bottom wall 102b. The rounded upper surface 124a of that boss functions as a valve seat. An outlet passage 126 extending through the boss and the housing bottom wall communicates with conduit 32 leading to catheter 16 (FIG. 1) or with conduit 92 leading to chamber 26 (FIG. 2). An inlet passage 128 is formed in the housing side wall 102c which communicates with conduit 32 or 92 leading from the fixed flow restrictor 36. A second conduit 132 extends from conduit 32 or 92 upstream from restrictor 36 through a radial passage 134 formed in divider wall 104 so that fluid at the delivery pressure fills the space inside bellows capsules 106 and 115.

As noted previously, the restrictor 38 provides adjustment of the flow rate through conduit 32 or 92 for a given pressure differential across it and automatic compensation to maintain this flow rate, given a specific range of deviations in the differential.

Fluid flows from restrictor 36 through conduit 32 into the lower chamber below the dividing wall 104. Then the fluid passes under the elastomeric valve seal 122 and through the outlet passage 126 resulting in the desired pressure drop and hence the desired flow rate across the seat before exiting the restrictor. The position of the plate 108 determines the compression force applied by spring 124 to plate 116 and the valve seal therein. The position of that plate therefore determines the set point and regulating pressure of the restrictor 38 which determines the flow rate to catheter 16 in the case of the FIG. 1 apparatus and to chamber 26 in the case of the FIG. 2 apparatus embodiment. A change in the vertical position of plate 108 changes the value of the restriction at the valve seat 124 and thus the flow rate. That position is changed by the step motor 72 which responds to command signals from microprocessor 68 as described above. These command signals cause the motor armature 112a to rotate in one direction or the other and its threaded engagement with the collar 110 moves the plate 108 up or down.

The restrictor 38 regulates flow rate by exposing the plate 116 to the fluid pressure in conduit 32 upstream of the fixed restrictor 36 as well as to the pressure in the housing 102 chamber below divider wall 104 (which is at the infusate chamber 24 pressure) and to the pressure at catheter 16 (FIG. 1) or chamber 26 (FIG. 2). Changes in these operating pressures change the forces exerted on the plate 116 and therefore on the valve seal 122 therein and so also on the restriction to fluid flow across the valve seat. Therefore, the ambient pressure changes which vary fluid flow also determine the relation between these three pressures so as to maintain the fluid flow rate constant at a given rate setting of the plate 108. Metal bellows capsules 106 and 115, of course, provide isolation of the fluid whose flow is being restricted from the motor 112. Also the conduit 132 allows volume displacement to and from the space inside those capsules during adjustment of fluid flow rate.

The variable restrictor illustrated in FIG. 3 allows the ability to choose and meter a wide range of extremely low fluid flow rates. Also, it has a relatively low volume displacement to the downstream side of the restrictor during its operation. Since the restrictor achieves fluid flow rate regulation passively, it does not consume appreciable electrical energy as it maintains the flow rate constant to the desired degree of accuracy with changes in internal and/or external ambient conditions. Electrical power is consumed only when energizing motor 112 to reset the restrictor to provide a different flow rate set point. Finally, the restrictor is quite simple in its operation and can be constructed in a relatively small size so that it fits easily within apparatus housing 12.

It will thus be seen that the present apparatus obtains very accurate control over the flow of infusate to the patient, which control is achieved at both ends of a very wide range. That flow is substantially independent of temperature changes to which the patient may be subjected. Also, the feedback loop in the apparatus compensates for most pressure changes. Once implanted in the patient, the apparatus can remain there for a prolonged period on the order of three years or more before the battery requires recharging or replacement. This is because the energy from the battery is only utilized intermittently at infrequent intervals to change and verify the infusate flow rate. While implanted, the apparatus can be refilled with infusate and recharged as necessary simply by injecting fresh infusate through the patient's skin directly into the apparatus.

The aforesaid attributes, in addition to the ability to program the patient's dosage schedule and to change that schedule by reprogramming when required and to monitor pump operation, make the present apparatus a very versatile device which should find wide use in patients requiring long-term infusion of medicants at different very low and very precise flow rates.

It will thus be seen that the objects set forth above, among those made apparent from the preceding description, are efficiently attained, and, since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described.

What is claimed as new and desired to be secured by Letters Patent of the United States is:

1. Variable flow implantable infusion apparatus comprising
   A. a housing;
   B. a variable volume infusate chamber in the housing;
   C. means for conducting infusate from said chamber to an infusion site outside the housing, said conducting means including series-connected fixed and electromechanically variable fluid flow restricting means;
   D. means in the housing for maintaining the contents in the infusate chamber under a substantially constant pressure;
   E. means for sensing the pressure differential across said fixed restricting means and producing indications in response thereto;
   F. programmable processing means in the housing which
      (1) sets the restriction of the variable flow restricting means at a selected programmed value,
      (2) samples the indications from the sensing means at selected programmed intervals,
      (3) compares each sample value with a reference value programmed into the processing means, and
      (4) issues a command signal for controlling the variable restricting means so as to maintain this constant selected infusate flow rate; and
   G. a battery for powering the variable restricting means and processing means.

2. The apparatus defined in claim 1 wherein said constant pressure maintaining means comprises a fluid energy storage cell.

3. The apparatus defined in claim 1 and further including a self-sealing penetrable septum mounted in the housing wall in fluid communication with the infusate chamber to permit said chamber to be refilled with infusate by percutaneous injection through the septum.

4. The apparatus defined in claim 1 wherein the sensing means comprises a differential fluid pressure transducer.

5. The apparatus defined in claim 4 wherein the sensing means further includes means for isolating the fluid flowing through the fixed restricting means from the transducer.

6. The apparatus defined in claim 1 and further including means in the housing for reprogramming the processing means so that infusate can be dispensed from the infusate chamber in accordance with selected different schedules.

7. The apparatus defined in claim 6 wherein the reprogramming means includes a telemetry receiver connected electrically to the microprocessor.

8. The apparatus defined in claim 1 wherein
   A. the conducting means also includes series-connected electromechanical valve means, and
   B. the microprocessor is programmed to issue command signals to close the valve means so as to prevent infusate flow from the infusate chamber to the infusion site when said flow differs from the preprogrammed flow rate for a selected number of samples; and
   C. the valve means also externally manually actuatable via a subdermal switch actuated by mechanical pressure or an external magnet brought into to said switch of the subdermal valve.

9. The apparatus defined in claim 1 wherein the processing means is programmed to change the reference flow value in accordance with a programmed schedule to vary the infusate flow rate from said chamber.

10. The apparatus defined in claim 1 and further including
    A. means for monitoring apparatus operations to develop operating data; and
    B. telemetry means for transmitting said data exteriorly of the body.

11. The apparatus defined in claim 1 and further including means in the housing electrically connected to the processing means and actuatable from outside the housing for selecting between a plurality of programmed flow rates.

12. The apparatus defined in claim 11 wherein the selecting means comprises a switch actuatable from outside the housing by an external magnet or by pressure on the skin under which the apparatus is implanted.

13. Variable flow implantable infusion apparatus comprising
A. a housing;
B. a variable volume infusate chamber in the housing;
C. means for conducting infusate from said chamber outside the housing;
D. a variable volume fluid pressure reservoir in the housing;
E. a variable volume fluid displacement reservoir in the housing;
F. a fluid path extending between the pressure reservoir and the displacement reservoir, said path including series-connected fixed and variable flow restricting means, said reservoirs and path arranged to be filled with a sustantially incompressible control fluid;
G. means in the housing for maintaining the contents of the pressure reservoir under substantially constant pressure;
H. means for sensing the fluid pressure differential across the fixed restricting means and producing indications in response thereto;
I. programmable processing means in the housing which
   (1) sets the restriction of the variable flow restricting means at a selected programmed value,
   (2) samples the indications from the sensing means at selected programmed intervals,
   (3) compares each sample value with a reference value programmed into the processing means, and
   (4) issues a command signal for controlling the variable restricting means so as to maintain this constant selected infusate flow rate; and
J. a battery for powering the variable restricting means and processing means.

14. The apparatus defined in claim 13 wherein said constant pressure maintaining means comprises a fluid energy storage cell.

15. The apparatus defined in claim 13 and further including a self-sealing penetrable septum mounted in the housing wall in fluid communication with the infusate chamber to permit said chamber to be refilled with infusate by percutaneous injection through the septum.

16. The apparatus defined in claim 13 and further including means in the housing for reprogramming the processing means so that infusate can be dispensed from the infusate chamber in accordance with selected different schedules.

17. The apparatus defined in claim 13 wherein
A. the conducting means includes series-connected electromechanical valve means, and
B. the microprocessor is programmed to issue command signals to close the valve means so as to prevent infusate flow from the infusate chamber when said flow differs from the preprogrammed flow rate for a selected number of samples; and
C. the valve means is also externally manually actuatable via a subdermal switch actuated by mechanical pressure or an external magnet brought into proximity to the subdermal valve.

18. The apparatus defined in claim 13 and further including
A. means for monitoring apparatus operations to develop operating data; and
B. telemetry means for transmitting said data exteriorly of the body.

19. The apparatus defined in claim 13 and further including means in the housing electrically connected to the processing means and actuatable from outside the housing for selecting between a plurality of programmed flow rates.

20. The apparatus defined in claim 1 or 13 wherein the variable flow restricting means comprises
A. a fluid container;
B. a fluid inlet passage into the container for connection to the downstream end of the fixed restricting means;
C. a fluid outlet passage from the container;
D. means in the housing defining a valve seat at the mouth of the outlet passage;
E. a restriction member in the container, said member being movable toward and away from the valve seat so as to variably restrict the flow of fluid from the inlet passage to the outlet passage;
F. means in the housing for establishing a restrictor reference position;
G. biasing means acting between the reference position establishing means and the restriction member for biasing the member toward the valve seat;
H. means for exposing
   (1) the surface of the restriction member distal to the valve seat only to the fluid pressure upstream from the fixed restricting means; and
   (2) the surface of the restriction member proximal to the valve seat only to the fluid pressure downstream from the fixed restricting means; and
I. means for varying the position of the reference position establishing means in accordance with the command signals from the processing means.

* * * * *